United States Patent
Maciuca et al.

(10) Patent No.: US 6,770,862 B1
(45) Date of Patent: Aug. 3, 2004

(54) SCALABLE WAFER INSPECTION

(75) Inventors: Dragos Maciuca, Castro Valley, CA (US); Natale M. Ceglio, Pleasanton, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/628,627

(22) Filed: Jul. 28, 2003

(51) Int. Cl.[7] .......................... H01L 27/00; G01N 21/88
(52) U.S. Cl. ............................. 250/208.1; 250/559.41; 250/559.45; 356/239.8; 356/237.4
(58) Field of Search .............................. 250/208.1, 239, 250/548, 559.4, 559.41–559.46; 356/239.7, 239.8, 237.2–237.5; 348/218.1, 295

(56) References Cited

U.S. PATENT DOCUMENTS

| | | | |
|---|---|---|---|
| 4,323,925 A | 4/1982 | Abell et al. | 358/213 |
| 5,065,245 A | 11/1991 | Carnall, Jr. et al. | 358/213.11 |
| 5,510,618 A | 4/1996 | Blecha et al. | 250/332 |
| 5,848,123 A | 12/1998 | Strommer | 378/98.8 |
| 5,872,364 A | 2/1999 | Strommer | 250/370.09 |
| 6,448,544 B1 * | 9/2002 | Stanton et al. | 250/208.1 |

FOREIGN PATENT DOCUMENTS

| | | |
|---|---|---|
| EP | 597934 | 8/1992 |
| EP | 776126 | 11/1996 |
| WO | WO 99/56113 | 4/1999 |

* cited by examiner

Primary Examiner—Kevin Pyo
(74) Attorney, Agent, or Firm—Luedeka, Neely & Graham, P.C.

(57) ABSTRACT

An imaging system for detecting defects on a substrate. Sensor module ports are disposed on an imaging platform. Sensor modules are removably connected to the sensor module ports, and are adapted to sense swaths on the surface of the substrate. Each of the sensor modules includes a time domain integration sensor, optics, an analog controller, and a digital controller. The time domain integration sensor optically senses the swath. The optics focus light from the swath on the time domain integration sensor. The analog controller receives signals from the time domain integration sensor and provides data signals. The digital controller receives the data signals, integrates the data signals into an image of the swath, and provides the image as digital signals to the sensor module port. A master controller receives the digital signals, composites them into a single image of a desired portion of the surface of the substrate, and detects defects within the image. A stage moves the substrate under the sensor modules under the control of the master controller, until the desired portion of the surface of the substrate has been imaged.

20 Claims, 3 Drawing Sheets

SCALABLE WAFER INSPECTION

FIELD

This invention relates to the field of optical inspection systems. More particularly, this invention relates to an inspection system that uses time delay integration sensors for optical inspection of integrated circuit substrates.

BACKGROUND

The integrated circuit fabrication industry relies on continual and repeated inspection of integrated circuits as they are produced to ensure that the processes are operating properly and that the integrated circuits themselves are properly formed. Automated visual inspection of integrated circuit substrates has become a standard step in this process. Automated visual inspection is accomplished by illuminating a substrate with light emanating from a controlled illuminator, and constructing an image of the surface based on the light that is reflected off the surface and toward a light sensor. The image is then processed to detect defects on the substrate surface.

Time delay integration sensors are often used as the optical sensor in automated substrate review. Time delay integration sensors tend to exhibit relatively lower noise and produce higher quality images than other types of sensors, especially under low light conditions. Thus, time delay integration sensors tend to exhibit a higher sensitivity to defects than other sensors, such as linear detection systems. This is because time delay integration techniques permit longer effective exposure times than linear detection sensors.

Integrated circuit substrate inspection has traditionally been performed using a system employing a single time delay integration module, consisting of the time delay integration sensor and associated electronic components that are mounted on a shared circuit board. The substrate, residing on a traveling stage, is indexed underneath the sensor in the x-direction. The sensor only resolves a partial width, or swath, of the substrate as it travels underneath the sensor on the stage. The sensor resolves a single image of the swath created during each pass of the substrate past the sensor. The substrate is then indexed in the y-direction and the sensor takes another image swath as the substrate travels back underneath the sensor in the x-direction. The process is repeated until as much of the substrate as desired, such as the entire substrate, has been imaged.

As the rate at which the production of integrated circuits increases, integrated circuit manufacturers look for ways to increase the speed at which the inspection processes are conducted. Typically, time delay integration systems have been sped up with the use of either a faster sensor which can handle increased stage indexing speeds, or a wider sensor that creates a wider swath and thus produces a larger image. However, these modifications require design and development of new supporting electronics and mechanical infrastructure for the automated inspection system. For example, speeding up the stage travel may require upgraded electronics to shift the active pixel line in the sensor at the increased rate. However, the sensor may not be able to adequately resolve images at the new rate. Installing a larger, faster, or more sensitive sensor also requires new supporting electronics, as well as hardware modifications. This design and development process is both expensive and time consuming.

What is needed, therefore, is a scalable time delay integration imaging system such that the effective speed at which the substrates are inspected can be readily increased as desired without new development.

SUMMARY

The above and other needs are met by a scalable imaging system adapted to detect defects on a surface of a substrate using time domain integration sensors. A plurality of sensor module ports are disposed on an imaging platform. Sensor modules are removably connected to the sensor module ports, where the sensor modules are adapted to optically sense swaths on the surface of the substrate. Each of the sensor modules includes a time domain integration sensor, optics, an analog controller, and a digital controller. The time domain integration sensor optically senses the swath, and has a first width. The optics focus light from the swath on the time domain integration sensor. The analog controller is disposed adjacent the time domain integration sensor and receives analog signals from the time domain integration sensor and provides data signals. The digital controller receives the data signals from the analog controller, integrates the data signals into an image of the swath, and provides the image as digital signals to the sensor module port. A master controller receives the digital signals from the sensor module ports, composites the digital signals into a single image of a desired portion of the surface of the substrate, and detects defects within the image of the desired portion of the surface of the substrate. A stage moves the substrate under the sensor modules under the control of the master controller, until the desired portion of the surface of the substrate has been imaged.

In this manner there is provided an instrument that is scalable in regard to the number of time delay integration sensor modules that are used during the inspection process. As few as one sensor module may be used, in which case an increased number of passes of the stage is required to image the entire surface of the substrate being inspected. However, additional sensor modules may be plugged in to the sensor module ports provided on the imaging platform, and when additional sensor modules are plugged in, the master controller automatically recognizes the additional sensor modules, and integrates the images which they produce into the overall image of the substrate that is produced. Thus, the number of substrate passes that is required to image the entire surface of the substrate is reduced with each additional sensor module that is added to the scalable instrument. However, recalibration or realignment or other difficult integration is not required, because each of the time delay integration sensor modules functions individually until a level at which the images that they produce are composited by the master controller.

In various preferred embodiments, the desired portion of the surface of the substrate is all of the surface of the substrate. Preferably, the swaths optically sensed by the sensor modules overlap one with another. The time domain integration sensors of the sensor modules are not aligned one with another in one embodiment, and in an alternate embodiment the time domain integration sensors of the sensor modules are aligned one with another. Preferably, the master controller is further adapted to automatically receive the digital signals from a new sensor module when it is connected to one of the sensor module ports and composite the digital signals into the image of the desired portion of the surface of the substrate. Increasing a number of sensor modules connected to the sensor module ports preferably decreases a number of passes of the stage required to image the desired portion of the surface of the substrate.

In one embodiment there is a given number of sensor module ports and the given number of sensor modules connected to the sensor module ports sufficient to image all of the surface of the substrate in a single pass of the stage. Preferably, the sensor module ports are disposed side by side in two lines disposed on either side of and parallel to a travel axis of the stage. Most preferably the sensor module ports are disposed side by side in two lines disposed on a left side and a right side of a travel axis of the stage. The sensor module ports on the left side are offset such that when all of the sensor module ports on the left side of the travel axis are filled with sensor modules, all of a left side of the surface of the substrate is imaged in a single pass of the stage Similarly, the sensor module ports on the right side are offset such that when all of the sensor module ports on the right side of the travel axis are filled with sensor modules, all of a right side of the surface of the substrate is imaged in a single pass of the stage.

Preferably, the time domain integration sensor, the optics, and the analog controller of a given one of the sensor modules are all disposed on a single circuit board and the digital controller of the one of the sensor modules is not disposed on the circuit board. The time domain integration sensor is preferably disposed along a given edge of the circuit board, and the time domain integration sensors of sensor modules disposed in adjacent sensor module ports are offset one from another by no more than a width of the time domain integration sensors.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
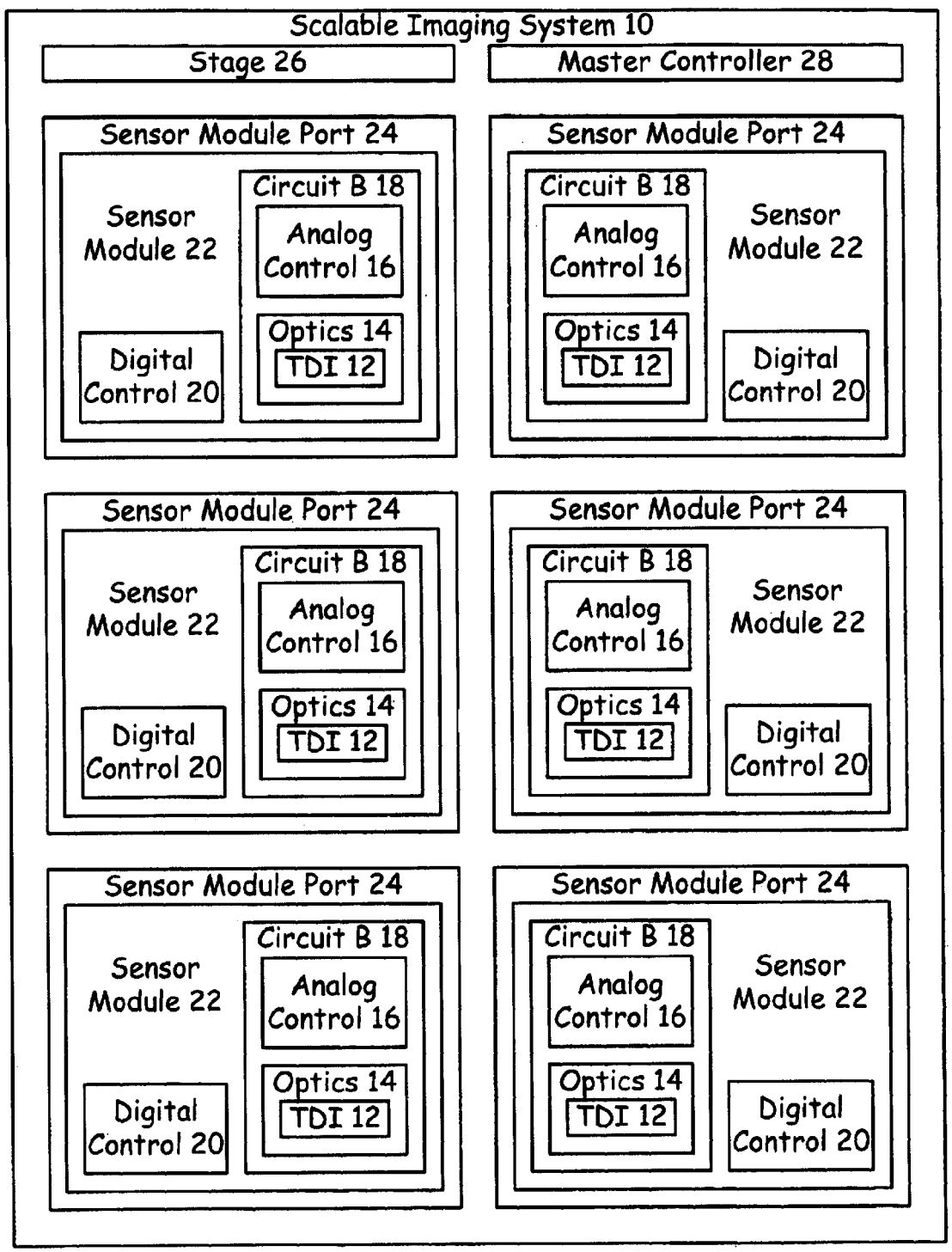
FIG. 1 is functional block diagram of a scalable inspection system according to a preferred embodiment of the present invention.

With reference now to FIG. 1, there is depicted a functional block diagram of a scalable imaging system 10 according to a preferred embodiment of the present invention. The scalable imaging system 10 utilizes one or more time domain integration sensors 12 to image a substrate as it is inspected by the imaging system 10. A stage 26 moves the substrate under the time domain integration sensors 12. With each pass of the stage 26, the time domain integration sensors 12 sense a swath of the substrate. When more time domain integration sensors 12 are used, fewer passes of the stage 26 are required to image a given portion of the substrate. Thus, when additional time domain integration sensors 12 are used, the time required to inspect a substrate is decreased. In other words, increasing the number of time domain integration sensors 12 used by the system 10 increases the effectual speed of the system 10. However, because of the modularity and expandability of the scalable imaging system 10, as described in more detail below, no additional development or other modification of the system 10 is required to achieve this effectual increase in inspection speed.

The scalable imaging system 10 is designed with a number of sensor module ports 24. As depicted in FIG. 1, the number of sensor module ports is six. However, this is by way of example only, and in various embodiments the scalable imaging system 10 may have any number of sensor module ports 24 that is greater than one. However, it is preferred that there be a sufficient number of sensor module ports 24 such that an entire substrate can be imaged in a single pass of the stage 26. Depending on the size of the substrate to be processed, this may require different numbers of sensor module ports 24, and it is understood that the current invention in its broadest form in not limited to any specific number of sensor module ports, as long as there are more than one.

The sensor module ports 24 are adapted to receive one sensor module 22 each. However, not every sensor module port 24 needs to have a sensor module 22 plugged in to it in order for the system 10 to function. The system 10 preferably functions with as few as one sensor module 22, although substrate inspection speed is increased when more than one sensor module 22 is used, as described elsewhere herein. Each sensor module 22 includes a digital controller 20, an analog controller 16, and a time domain integration sensor 12. The sensor module 22 also preferably includes optics 14 as may be necessary or desirable to focus the light coming from a substrate onto the time domain integration sensor 12, regardless of whether that light is reflected off of, emanating from, or transmitted through the surface of the substrate.

The time domain integration sensor 12 and analog controller 16, and optics 14 if present, are preferably all mounted on a single circuit board 18. The digital controller 20 is preferably not mounted on the circuit board 18, so that the circuit board 18 can be as small as possible, for reasons as described in more detail hereafter. It is preferred that the time domain integration sensor 12 and the analog controller 16 be mounted on a common circuit board, and that they be in near proximity one to another, so that the overall quality of the images produced by the time domain integration sensor 12 is generally improved. The signals produced by the time domain integration sensor 12 tend to be weak and at a high frequency. Thus, the signals tend to degrade rather quickly. If the distance between the time domain integration sensor 12 and the analog controller 16 is too great, then the signal tends to degrade to too great an extent, and the signal to noise ratio falls dramatically. Thus, by placing the analog controller 16 in near proximity to the time domain integration sensor 12 on the circuit board 18, the amplifiers in the analog controller 16 boost the signals from the time domain integration sensor 12 before the signal is too degraded.

The analog controller 16 also preferably controls functions such as indexing the active pixel line in the time domain integration sensor 12, preferably at the same rate of speed as the stage 26 is moving the substrate beneath the time domain integration sensor 12. The analog controller 16 preferably sends the amplified signals to the digital controller 20, which integrates the signals from the analog controller 16 into an image of the swath of the substrate that is resolved by the associated time domain integration sensor 12. The digital controller 20 then sends the image signals through the sensor module port 24.

The signals sent through the sensor module ports 24 are received by a master controller 28, which receives all of the signals from as many sensor modules 22 as may be plugged in to the system 10. The master controller 28 composites all of the images received from the various sensor modules 22 into an image of the surface of the substrate. If there are not enough sensor modules 22 to image all of the desired portion of the surface of the substrate in a single pass, then the master controller 28 directs the stage 26 to shift the substrate as appropriate and pass the substrate underneath the time domain integration sensors 12 again. This process is repeated as necessary until all of the desired portion of the surface of the substrate has been inspected. The master controller 28 then either passes the signals off to another system for defect analysis, or performs defect analysis of the substrate itself.

Because the master controller 28 is designed from the onset to recognize additional sensor modules 22 as they are plugged in to the system 10, regardless of which sensor module port 24 they are plugged in to, and to automatically integrate the signals from the sensor modules 22 when they are available, no redesign or development is required to increase the effective speed of the system 10. Instead, more sensor modules 22 may simply be plugged into the system 10 to increase its effective analysis speed. For example, a fabrication unit having initially low throughputs may opt to purchase a system 10 with a single sensor module 22, because even with one sensor module 22 the system 10 is able to keep up with the production schedule. However, as the production schedule increases and the inspection time of the substrates becomes more of an issue, additional sensor modules 22 can be purchased as needed to keep up with the inspection schedule.

As another example, a system 10 can be purchased with sufficient sensor modules 22 to resolve all of the surface of a substrate with a given size, such as a six inch diameter. However, if it is later desired to inspect eight, ten, or twelve inch diameter substrates, additional sensor modules 22 can be added to the system 10 so that all of the surface of a substrate of a larger size can be inspected in a single pass, or in a reduced number of passes. Thus, the scalable imaging system 10 according to the present invention as described provides many benefits that are not found in the inspection systems of the prior art.

Figure 2:
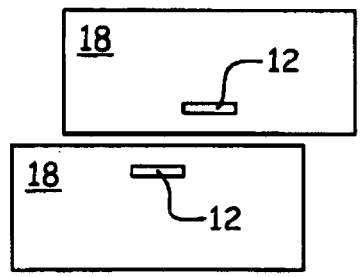
FIG. 2 is a top plan view of a first embodiment of an alignment of sensors in the scalable inspection system.

FIG. 2 depicts how two different time domain integration sensors 12 could be aligned. In this embodiment the time domain integration sensors 12 are disposed on one edge of identical circuit boards 18. However, as mounted in the system 10, the time domain integration sensors 12 are offset, so that they resolve different swaths on the substrate. The swaths may be either separate one from another, adjacent, or overlapping, as desired. In a most preferred embodiment, there is some small degree of overlap between swaths so that the resultant composited image is well aligned and has no gaps. By making the circuit boards 18 and other parts of the sensor modules 22 identical, only a single configuration of a sensor module 22 needs to be produced and inventoried, and any sensor module 22 can be plugged in to any position in the system 10.

Figure 3:
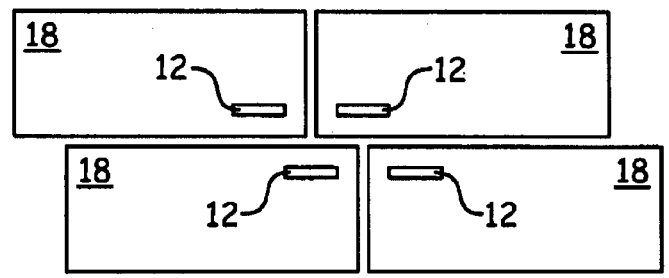
FIG. 3 is a top plan view of a second embodiment of an alignment of sensors in the scalable inspection system.

FIG. 3 depicts an alternate embodiment with four circuit boards 18, with the time domain integration sensors 12 disposed in the corners of the circuit boards 18. In this embodiment there are two different sensor board 18 configurations, which means that two different sensor module 22 configurations must be produced and inventoried, and the different sensor module 22 configurations may not all fit in the same sensor module ports 24. However, one advantage of the configuration as depicted in FIG. 3 is that there is very little distance between the time domain integration sensors 12 of adjacent rows of circuit boards 18, and thus the stage 26 does not have to travel so far to scan the substrate past the time domain integration sensors 12.

Figure 4:
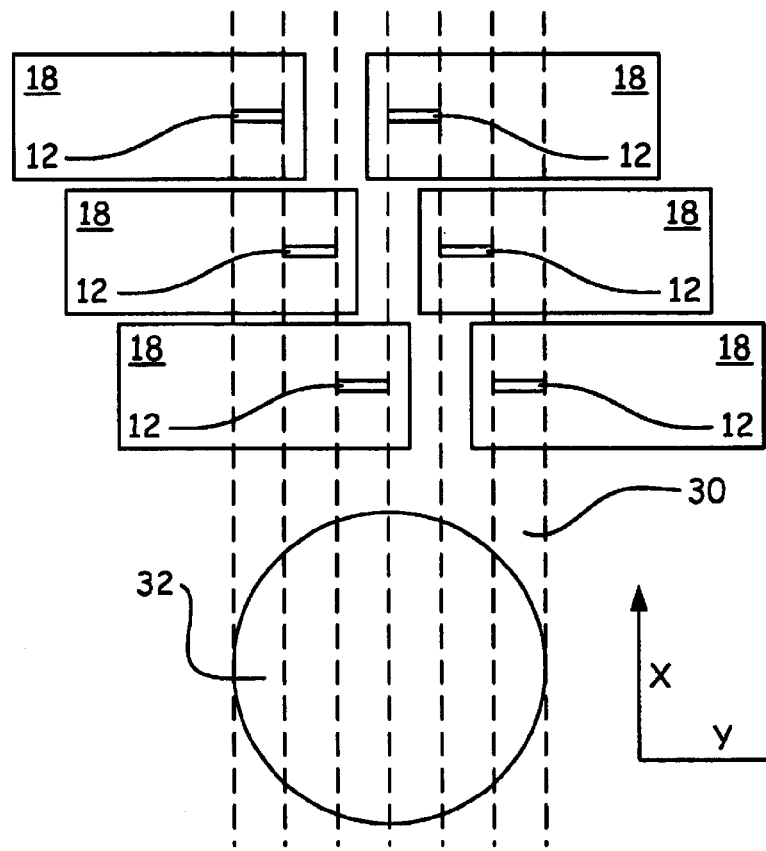
FIG. 4 is a top plan view of a third embodiment of an alignment of sensors in the scalable inspection system.
Figure 5:
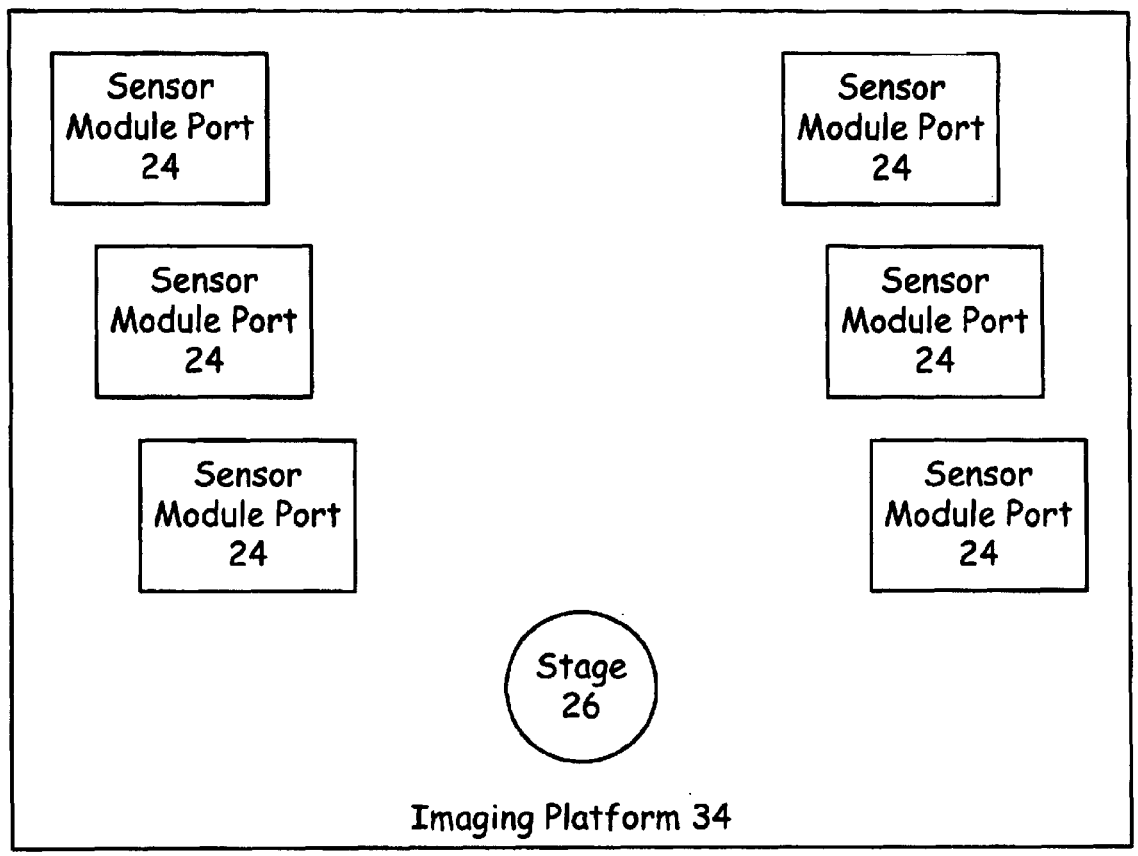
FIG. 5 is a top plan view of the staggered sensor ports of the scalable inspection system.

FIG. 4 depicts yet another embodiment of the system 10, which has six circuit board 18, all of which are identical, with the time domain integration sensor 12 disposed at one end of the circuit board 18, and centered. As depicted, the time domain integration sensors 12 are preferably offset one from another when they are mounted in the system 10. Most preferably, all of the sensor modules 22 are identical, and the time domain integration sensors 12 become offset one from another because of the placement of the sensor module ports 24, such as depicted in FIG. 5. FIG. 4 depicts an embodiment where the swaths 30 of the time domain integration sensors are adjacent one another, and where there are sufficient time domain integration sensors 12 to resolve all of the surface of the substrate 32 in a single pass of the stage 26. As used herein, the X direction as indicated is the direction of stage 26 travel during a sensing operation, and the Y direction as indicated is the direction in which the stage 26 may need to index the substrate 32 if there are not enough time domain integration sensors 12 to resolve all of the desired portion of the substrate 32 in a single pass.

Figure 6:
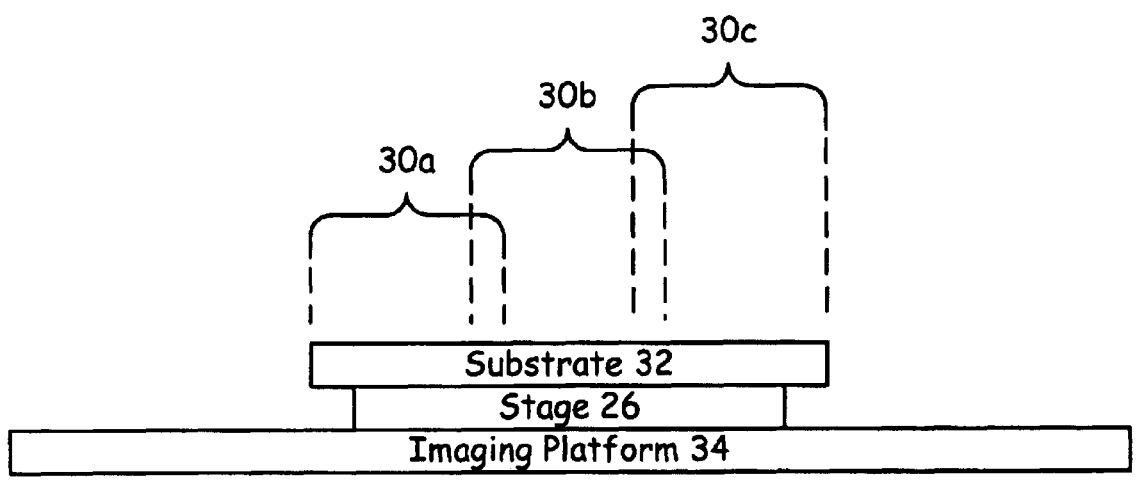
FIG. 6 is a side view of the overlapping swaths imaged by the sensor modules of the scalable inspection system.

FIG. 6 depicts a side view of the substrate 32 on the stage 26, mounted to an imaging platform 34 of the system 10. As depicted in FIG. 5, the imaging platform 34 in one embodiment determines the offset between adjacent sensor modules 22, by specifying the offset between the sensor module ports 24, into which the sensor modules 22 are inserted. FIG. 6 depicts an embodiment in which adjacent swaths 30 a–c are overlapping.

Another benefit of the scalable imaging system 10 of the present invention is that the time domain integration sensors 12 do not necessarily need to be aligned one to another, because they all have separate analog controllers 16 and digital controllers 20. However, it is still preferred that all of the time domain integration sensors 12 be aligned relative to the travel of the stage 26.

The sensor module 22 preferably occupies a width that is no larger than about the width of the circuit board 18. In this manner, the size of the sensor module 22 does not physically prevent the sensor modules 22 from being placed relatively close to one another in the system 10. This is also why the digital controller 20, which tends to be rather large in size, is not mounted on the circuit board 18. In this manner, the circuit board 18 can be kept relatively small in size, which allows the overall size of the sensor module 22 to be keep commensurately small in size. In a most preferred embodiment, the width of the circuit board 18 is no greater than that required by the time domain integration sensor 12. In this manner, the sensor modules 22 may be placed as close together as allowed by the widths of the time domain integrations sensors 12.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A scalable imaging system adapted to detect defects on a surface of a substrate using time domain integration sensors, the scalable imaging system comprising:
   an imaging platform having a plurality of sensor module ports adapted to receive sensor modules,
   a sensor module removably connected to one of the sensor module ports, the sensor module adapted to optically sense swaths on the surface of the substrate, the sensor module including,
      a time domain integration sensor adapted to optically sense the swath, the time domain integration sensor having a first width,
         optics adapted to focus light from the swath on the time domain integration sensor,
         an analog controller disposed adjacent the time domain integration sensor and adapted to receive analog signals from the time domain integration sensor and provide data signals, and
         a digital controller adapted to receive the data signals from the analog controller, integrate the data signals into an image of the swath, and provide the image as digital signals to the sensor module port,
   a master controller adapted to receive the digital signals from the sensor module ports, composite the digital signals into a single image of a desired portion of the surface of the substrate, and to detect defects within the image of the desired portion of the surface of the substrate, and
   a stage adapted to move the substrate under the sensor modules under the control of the master controller, until the desired portion of the surface of the substrate has been imaged.

2. The scalable imaging system of claim 1, wherein the desired portion of the surface of the substrate is all of the surface of the substrate.

3. The scalable imaging system of claim 1, wherein swaths optically sensed by adjacent sensor modules overlap one with another.

4. The scalable imaging system of claim 1, wherein the time domain integration sensors of adjacent sensor modules are not aligned one with another.

5. The scalable imaging system of claim 1, wherein the time domain integration sensors of adjacent sensor modules are aligned one with another.

6. The scalable imaging system of claim 1, wherein the master controller is further adapted to automatically receive the digital signals from an additional sensor module when it is connected to one of the sensor module ports and composite the digital signals from the additional sensor module into the image of the desired portion of the surface of the substrate.

7. The scalable imaging system of claim 1, wherein increasing a number of sensor modules connected to the sensor module ports decreases a number of passes of the stage required to image the desired portion of the surface of the substrate.

8. The scalable imaging system of claim 1, comprising a given number of sensor module ports and the given number of sensor modules connected to the sensor module ports sufficient to image all of the surface of the substrate in a single pass of the stage.

9. The scalable imaging system of claim 1, wherein the sensor module ports are disposed side by side in two lines disposed on either side of a travel axis of the stage.

10. The scalable imaging system of claim 1, wherein the sensor module ports are disposed side by side in two lines disposed on a left side and a right side of a travel axis of the stage, and the sensor module ports on the left side are offset such that when all of the sensor module ports on the left side of the travel axis are filled with sensor modules, all of a left side of the surface of the substrate is imaged in a single pass of the stage, and the sensor module ports on the right side are offset such that when all of the sensor module ports on the right side of the travel axis are filled with sensor modules, all of a right side of the surface of the substrate is imaged in a single pass of the stage.

11. The scalable imaging system of claim 1, wherein the time domain integration sensor, the optics, and the analog controller of the sensor module are all disposed on a single circuit board and the digital controller of the sensor module is not disposed on the circuit board.

12. The scalable imaging system of claim 1, wherein the time domain integration sensor, the optics, and the analog controller of the sensor module are all disposed on a single circuit board, and the time domain integration sensor is disposed along an edge of the circuit board, and the time domain integration sensors of sensor modules disposed in adjacent sensor module ports are offset one from another by no more than a width of the time domain integration sensors.

13. A scalable imaging system adapted to detect defects on a surface of a substrate using time domain integration sensors, the scalable imaging system comprising:
   an imaging platform having a plurality of sensor module ports, the sensor module ports disposed side by side on either side of a travel axis of the substrate through the scalable imaging system,
   sensor modules removably connected to the sensor module ports, the sensor modules adapted to optically sense swaths on the surface of the substrate, wherein the swaths optically sensed by the sensor modules overlap one with another, each of the sensor modules including,
      a time domain integration sensor adapted to optically sense the swath, the time domain integration sensor having a first width,
      optics adapted to focus light from the swath on the time domain integration sensor,
      an analog controller disposed adjacent the time domain integration sensor and adapted to receive analog signals from the time domain integration sensor and provide data signals, and
      a digital controller adapted to receive the data signals from the analog controller, integrate the data signals into an image of the swath, and provide the image as digital signals to the sensor module port,
   a master controller adapted to receive the digital signals from the sensor module ports, composite the digital signals into a single image of a desired portion of the surface of the substrate, and to detect defects within the image of the desired portion of the surface of the substrate, and
   a stage adapted to move the substrate under the sensor modules under the control of the master controller, until the desired portion of the surface of the substrate has been imaged.

14. The scalable imaging system of claim 13, comprising a given number of sensor module ports and the given number of sensor modules connected to the sensor module ports sufficient to image all of the surface of the substrate in a single pass of the stage.

15. The scalable imaging system of claim 13, wherein the sensor module ports are disposed on a left side and a right side of a travel axis of the stage, and the sensor module ports on the left side are offset such that when all of the sensor module ports on the left side of the travel axis are filled with sensor modules, all of a left side of the surface of the substrate is imaged in a single pass of the stage, and the sensor module ports on the right side are offset such that when all of the sensor module ports on the right side of the travel axis are filled with sensor modules, all of a right side of the surface of the substrate is imaged in a single pass of the stage.

16. The scalable imaging system of claim 13, wherein the time domain integration sensor, the optics, and the analog controller of a given one of the sensor modules are all disposed on a single circuit board and the digital controller of the one of the sensor modules is not disposed on the circuit board.

17. A scalable imaging system adapted to detect defects on a surface of a substrate using time domain integration sensors, the scalable imaging system comprising:

an imaging platform having a plurality of sensor module ports, the sensor module ports disposed on a left side and a right side of a travel axis of the substrate through the scalable imaging system, and the sensor module ports on the left side are offset such that when all of the sensor module ports on the left side of the travel axis are filled with sensor modules, all of a left side of the surface of the substrate is imaged in a single pass, and the sensor module ports on the right side are offset such that when all of the sensor module ports on the right side of the travel axis are filled with sensor modules, all of a right side of the surface of the substrate is imaged in a single pass, the sensor modules removably connected to the sensor module ports, the sensor modules adapted to optically sense swaths on the surface of the substrate, wherein the swaths optically sensed by the sensor modules overlap one with another, each of the sensor modules including, a time domain integration sensor adapted to optically sense the swath, the time domain integration sensor having a first width, optics adapted to focus light from the swath on the time domain integration sensor, an analog controller disposed adjacent the time domain integration sensor and adapted to receive analog signals from the time domain integration sensor and provide data signals, and a digital controller adapted to receive the data signals from the analog controller, integrate the data signals into an image of the swath, and provide the image as digital signals to the sensor module port, wherein the time domain integration sensor, the optics, and the analog controller are all disposed on a single circuit board and the digital controller is not disposed on the circuit board, a master controller adapted to receive the digital signals from the sensor module ports, composite the digital signals into a single image of a desired portion of the surface of the substrate, and to detect defects within the image of the desired portion of the surface of the substrate, and a stage adapted to move the substrate under the sensor modules under the control of the master controller, until the desired portion of the surface of the substrate has been imaged.

18. The scalable imaging system of claim 17, wherein the desired portion of the surface of the substrate is all of the surface of the substrate.

19. The scalable imaging system of claim 17, comprising a given number of sensor module ports and the given number of sensor modules connected to the sensor module ports sufficient to image all of the surface of the substrate in a single pass of the stage.

20. The scalable imaging system of claim 17, wherein the swaths optically sensed by the sensor modules overlap one with another.

* * * * *

UNITED STATES PATENT AND TRADEMARK OFFICE
CERTIFICATE OF CORRECTION

PATENT NO. : 6,770,862 B1
DATED : August 3, 2004
INVENTOR(S) : Dragos Maciuca and Natale M. Ceglio It is certified that error appears in the above-identified patent and that said Letters Patent is hereby corrected as shown below:

Column 1,
Line 2, below the title, insert:
-- The U.S.Government has a paid-up license in this invention and the right in limited circumstances to require the patent owner to license others on reasonable terms as provided for by the terms of contract number 70NANB0H3038 awarded by NIST. --

Signed and Sealed this

Second Day of August, 2005

JON W. DUDAS
*Director of the United States Patent and Trademark Office*